(12) United States Patent
Koseki et al.

(10) Patent No.: US 10,450,541 B2
(45) Date of Patent: Oct. 22, 2019

(54) CELL CULTURE APPARATUS

(71) Applicant: TOYO SEIKAN GROUP HOLDINGS, LTD., Tokyo (JP)

(72) Inventors: Osamu Koseki, Tokyo (JP); Ryo Suenaga, Yokohama (JP); Ken Kashiwabara, Yokohama (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 246 days.

(21) Appl. No.: 15/510,447

(22) PCT Filed: Sep. 9, 2015

(86) PCT No.: PCT/JP2015/004591
§ 371 (c)(1),
(2) Date: Mar. 10, 2017

(87) PCT Pub. No.: WO2016/042743
PCT Pub. Date: Mar. 24, 2016

(65) Prior Publication Data
US 2017/0260489 A1    Sep. 14, 2017

(30) Foreign Application Priority Data

Sep. 17, 2014 (JP) .................. 2014-189273
Sep. 17, 2014 (JP) .................. 2014-189274
(Continued)

(51) Int. Cl.
*C12M 1/34* (2006.01)
*C12M 3/00* (2006.01)
(Continued)

(52) U.S. Cl.
CPC ............ *C12M 23/48* (2013.01); *C12M 23/04* (2013.01); *C12M 23/34* (2013.01); *C12M 23/50* (2013.01);
(Continued)

(58) Field of Classification Search
CPC ...... C12M 23/04; C12M 41/14; C12M 41/36; C12M 23/48; C12M 23/50
See application file for complete search history.

(56) References Cited

U.S. PATENT DOCUMENTS 7,754,478 B2    7/2010  Suzuki et al.
9,752,112 B2    9/2017  Watanabe et al.
(Continued)

FOREIGN PATENT DOCUMENTS

CN  103992946 A    8/2014
JP  11-509420 A    8/1999
(Continued)

OTHER PUBLICATIONS

English Machine Translation of JP 2014-079177A, publication dated May 8, 2014.
(Continued)

*Primary Examiner* — William H. Beisner
(74) *Attorney, Agent, or Firm* — Sughrue Mion, PLLC (57) ABSTRACT

A cell culture apparatus including cell culture units U and a measurement part (5). The measurement part (5) is provided with an imaging part (51) and is disposed so as to be capable of moving up and down between a back panel part (21) of a casing (2) and a culture container accommodating shelf (32). When the measurement unit (5) reaches a measurement position of each cell culture unit U which is a measurement subject, the culture container accommodating shelf (32) slides toward the measurement unit (5) so that portions to be
(Continued)

measured of culture containers U20, U30 in each cell culture unit U come in an imaging range of the imaging part (51).

10 Claims, 9 Drawing Sheets

(30) Foreign Application Priority Data

Sep. 17, 2014 (JP) ................................ 2014-189275
Sep. 17, 2014 (JP) ................................ 2014-189276

(51) Int. Cl.
*C12M 1/12* (2006.01)
*C12M 1/00* (2006.01)
*C12M 1/26* (2006.01)
*C12M 3/06* (2006.01)

(52) U.S. Cl.
CPC ............ *C12M 27/16* (2013.01); *C12M 33/12* (2013.01); *C12M 41/14* (2013.01); *C12M 41/36* (2013.01)

(56) References Cited

U.S. PATENT DOCUMENTS

| | | | |
|---|---|---|---|
| 9,951,305 | B2 | 4/2018 | Kobayashi et al. |
| 2007/0148764 | A1 | 6/2007 | Suzuki et al. |
| 2009/0042293 | A1 | 2/2009 | Hata et al. |
| 2010/0075406 | A1 | 3/2010 | Tanaka et al. |
| 2012/0156768 | A1 | 6/2012 | Watanabe et al. |
| 2013/0210130 | A1* | 8/2013 | Larcher ................. C12M 23/44 435/288.7 |
| 2014/0087455 | A1 | 3/2014 | Kobayashi et al. |
| 2014/0335608 | A1 | 11/2014 | Tanaka et al. |
| 2015/0218503 | A1 | 8/2015 | Kiyama et al. |
| 2017/0015965 | A1 | 1/2017 | Hata |
| 2017/0327780 | A1 | 11/2017 | Watanabe et al. |

FOREIGN PATENT DOCUMENTS

| | | |
|---|---|---|
| JP | 2014-79177 A | 5/2014 |
| KR | 20-0263386 Y1 | 2/2002 |
| KR | 10-2007-0006680 A | 1/2007 |
| KR | 10-2013-0124408 A | 11/2013 |
| WO | 97/04074 A1 | 2/1997 |
| WO | 2007/052716 A1 | 5/2007 |
| WO | 2008/136371 A1 | 11/2008 |
| WO | 2011/130865 A2 | 10/2011 |
| WO | 2013/114845 A1 | 8/2013 |
| WO | 2014/033889 A1 | 3/2014 |
| WO | 2014/049701 A1 | 4/2014 |
| WO | 2015/145954 A1 | 10/2015 |

OTHER PUBLICATIONS

International Preliminary Report on Patentability with translation of Written Opinion dated Mar. 30, 2017, issued by the International Searching Authority in application No. PCT/JP2015/004591.
Communication dated May 2, 2018, from European Patent Office in counterpart application No. 15841995.2.
International Search Report of PCT/JP2015/004591, dated Dec. 15, 2015 (PCT/ISA/210).

* cited by examiner

CELL CULTURE APPARATUS

CROSS REFERENCE TO RELATED APPLICATIONS

This Application is a U.S. National Stage of Application No. PCT/JP2015/004591, filed on Sep. 9, 2015. Priority under 35 U.S.C.§ 119(a) and 35 U.S.C.§ 365(b) is claimed from Japanese Patent Application No. 2014-189273 filed on Sep. 17, 2014, Japanese Patent Application No. 2014-189274 filed on Sep. 17, 2014, Japanese Patent Application No. 2014-189275 filed on Sep. 17, 2014 and Japanese Patent Application No. 2014-189276 filed on Sep. 17, 2014, the disclosures of which are incorporated herein by reference in their entirety.

FIELD

The present invention relates to a cell culture apparatus.

BACKGROUND

In recent years, it has been required that cells, tissues or the like are efficiently cultured in large amounts under an artificial environment in fields of production of medicines, gene therapy, regenerative therapy, immunotherapy and the like.

In such cell culture, a medium container to supply a medium to a culture container and the culture container for use in cell culture are connected by a tube to constitute a cell culture unit, and the cell culture is performed in a closed system by use of this cell culture unit, thereby avoiding a risk of contamination to proliferate the cells.

In this cell culture unit, the medium is generally required to be refrigerated, and hence the medium container is stored in a cold insulation chamber. Furthermore, in the cell culture, it is necessary to control a temperature, air environment and the like, and hence the culture container is stored in an incubator. Then, the medium is transferred from the medium container to the culture container via the tube.

Alternatively, for example, in Patent Literature 1, a cell culture apparatus is disclosed in which such culture units are stored in a multi-stage state and cell culture is performed.

RELATED ART DOCUMENT

Patent Literature

Patent Literature 1: WO 2007/052716

SUMMARY

Technical Problem

However, in a culture apparatus described in Patent Literature 1, for the purpose of observing the number and others of cells proliferated in a culture container (a culture bag), the cells in the culture container are guided to another container (a cell inoculation cassette or a dummy cassette) and imaged by using a CCD camera. In addition, all culture units have a similar constitution, and a complicated apparatus constitution is taken.

The present invention has been developed in view of the above circumstances, and an object thereof is to provide a cell culture apparatus in which a plurality of cell culture units each comprising culture containers to which a medium is supplied together with cells to perform cell culture and a medium container to supply the medium to the culture containers are stored in a multi-stage state, and when cell culture is individually performed in each of the cell culture units, a progressive state of the cell culture in all the cell culture units can be measured by a single measurement unit.

Solution to Problem

To achieve the above object, the present invention is directed to a cell culture apparatus in which there are stored, in a multi-stage state in a casing, a plurality of cell culture units each comprising at least a culture container to which a medium is supplied together with cells to perform cell culture and a medium container to supply the medium to the culture container, the culture container and the medium container being connected by a transfer tube, thereby individually performing the cell culture in each of the cell culture units, wherein a support frame in which a plurality of slide rails are arranged in a multi-stage state along a height direction is disposed in the casing, a culture container accommodating shelf in which the culture containers are accommodated is slidably attached to each of the slide rails, a measurement unit comprising an imaging part is disposed so as to be movable up and down between a back panel part of the casing and the culture container accommodating shelf, and when the measurement unit reaches a measurement position of each cell culture unit that is a measurement subject, the culture container accommodating shelf which accommodates the culture containers provided in the cell culture unit moves toward the measurement unit so that portions to be measured of the culture containers provided in the cell culture unit come in an imaging range of the imaging part.

According to such a constitution, the plurality of cell culture units each comprising the culture containers and the medium container are stored in the multi-stage state, and when the cell culture is individually performed in each of the cell culture units, a progressive state of the cell culture in the cell culture unit of the measurement subject can be measured by a single measurement unit in each of all the cell culture units without interfering with an adjacent cell culture unit.

Furthermore, in a culture apparatus described in Patent Literature 1 mentioned above, a medium container (a medium bag) and a culture container (a culture bag) are stored in the same thermostatic tank, so cell culture cannot be performed under a temperature environment suitable for each of these containers.

In view of the above circumstances, the present invention can have the following constitution to provide a cell culture apparatus in which a plurality of cell culture units each comprising culture containers to which a medium is supplied together with cells to perform cell culture and a medium container to supply the medium to the culture containers are stored in a multi-stage state, and when the cell culture is individually performed in each of the cell culture units, the cell culture can efficiently be performed under a temperature environment suitable for each of the culture containers and the medium container.

That is, the cell culture apparatus according to the present invention may have a constitution comprising an incubating tank in which the culture containers are stored and a cold insulation tank in which the medium container is stored, wherein in each of the incubating tank and the cold insulation tank, there are disposed an incubating tank side support frame and a cold insulation tank side support frame in each of which a plurality of slide rails are arranged in a multi-stage state along a height direction, the culture container accommodating shelf is slidably attached to each of the slide rails arranged in the multi-stage state in the incubating tank side support frame, and a medium container accommodating shelf to accommodate the medium container is slidably attached to each of the slide rails arranged in the multi-stage state in the cold insulation tank side support frame, and the culture container accommodating shelf and the medium container accommodating shelf form a pair and are disposed separately in the incubating tank and the cold insulation tank.

According to such a constitution, the plurality of cell culture units each comprising the culture containers and the medium container are stored in a multi-stage state, and when the cell culture is individually performed in each of the cell culture units, the cell culture can efficiently be performed under the temperature environment suitable for each of the culture containers and the medium container.

Alternatively, the medium container and the culture containers are connected by the tube to constitute the cell culture unit, and when the cell culture is performed in a closed system, bubbles might enter into the culture containers in a process of the cell culture, for example, at a time of supplying the medium from the medium container to the culture containers. When the bubbles enter into the culture containers, it is feared that a culture environment in the culture container does not become uniform, and an efficiency of the cell culture deteriorates. It is also considered that, when a content is taken out from the culture container after the cell culture is ended, the liquid delivery is disturbed by the bubbles, but in the culture apparatus described in Patent Literature 1 mentioned above, these problems are not taken into consideration at all.

For example, it is considered that the bubbles flow into the medium container or the like which forms the closed system together with the culture container, for the purpose of removing the bubbles which enter into the culture container while maintaining the closed system. However, when a timing to end an operation of removing the bubbles is wrong, the bubbles might remain in the culture containers, and the contents of the culture containers might flow into the medium container or the like.

In view of the above circumstances, the present invention can have the following constitution to provide a cell culture apparatus in which a cell culture unit comprising culture containers to which a medium is supplied together with cells to perform cell culture and a medium container to supply the medium to the culture containers is stored, and when the cell culture is performed in this cell culture unit and when an operation of removing bubbles which enter into the culture containers in a process of the cell culture is performed, a timing to end the operation can be judged.

That is, the cell culture apparatus according to the present invention may have a constitution in which the culture container accommodating shelf or the medium container accommodating shelf comprises weight detecting means, and in removing bubbles which enter into the culture containers in the process of the cell culture, the bubbles are transferred to the medium container through the transfer tube, and the weight detecting means provided in the culture container accommodating shelf or the medium container accommodating shelf detects a weight change of the culture container or the medium container to end a transfer operation of the bubbles.

According to such a constitution, the cell culture unit comprising the culture containers and the medium container is stored, and when the cell culture is performed in this cell culture unit and when an operation of removing the bubbles which enter into the culture containers in the process of the cell culture is performed, the timing to end the operation can be judged and the operation can automatically or manually be ended.

Furthermore, when the contents of the culture containers are taken outside in addition to removing the bubbles which enter into the culture containers in the process of the cell culture, it is required that the contents are inhibited from remaining, but in the above-mentioned culture apparatus described in Patent Literature 1, these problems are not taken into consideration at all.

In view of the above circumstances, the present invention can have the following constitution to provide a cell culture apparatus in which there is stored a cell culture unit comprising culture containers to which a medium is supplied together with cells to perform cell culture and a medium container to supply the medium to the culture containers, and when the cell culture is performed in this cell culture unit, bubbles which enter into the culture containers in a process of the cell culture are easily removed, and when contents of the culture containers are taken outside, the contents can be inhibited from remaining in the culture containers.

That is, the cell culture apparatus according to the present invention may have a constitution in which the culture container accommodating shelf comprises tilting means for tilting the culture containers so that ports for liquid delivery provided in the culture containers are positioned at lower positions or upper positions.

According to such a constitution, the cell culture unit comprising the culture containers and the medium container is stored, and when the cell culture is performed in this cell culture unit, the bubbles which enter into the culture containers in the process of the cell culture can easily be removed, and when the contents of the culture containers are taken outside, the contents can be inhibited from remaining.

Advantageous Effects of Invention

According to the present invention, a plurality of cell culture units each comprising culture containers and a medium container are stored in a multi-stage state, and when cell culture is individually performed in each of the cell culture units, a progressive state of the cell culture in each cell culture unit that is a measurement subject can be measured by a single measurement unit in each of all the cell culture units without interfering with an adjacent cell culture unit.

DETAILED DESCRIPTION

Hereinafter, a preferable embodiment of a cell culture apparatus according to the present invention will be described with reference to the drawings.

Figure 1:
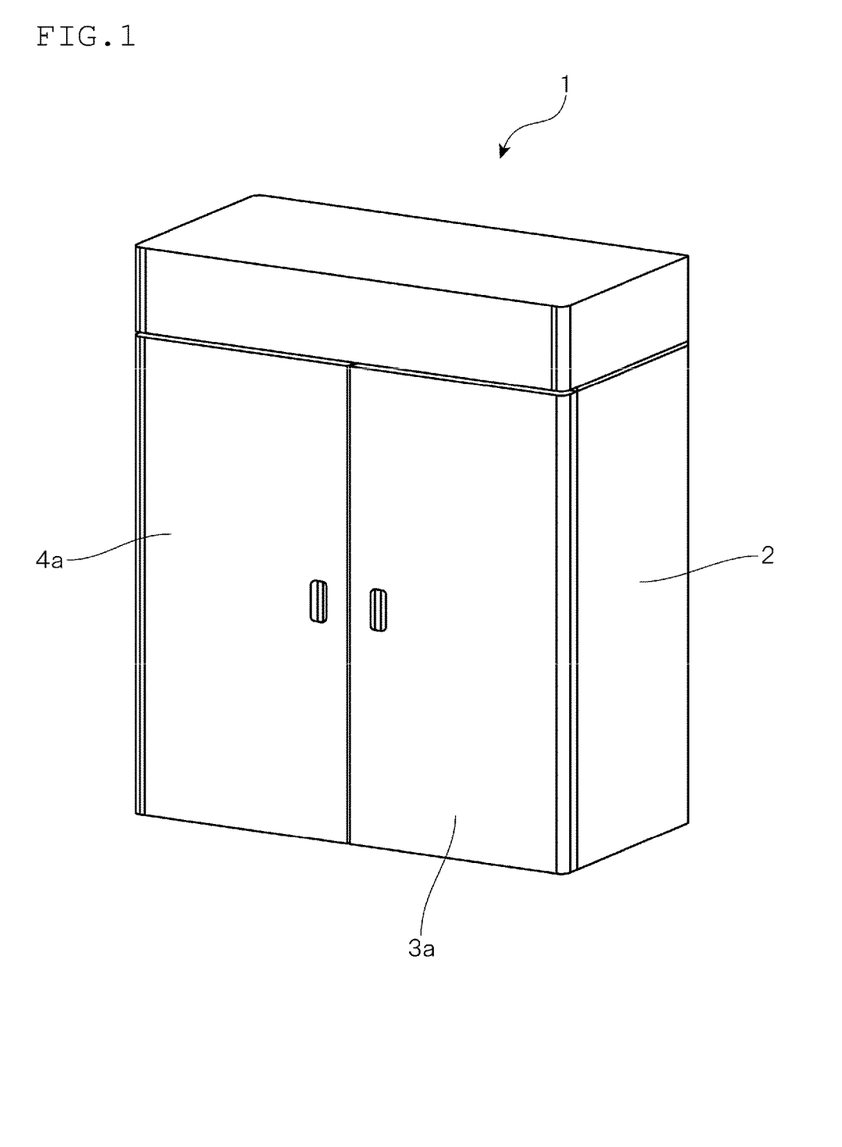
FIG. 1 is an appearance schematic view of a cell culture apparatus according to an embodiment of the present invention.
Figure 2:
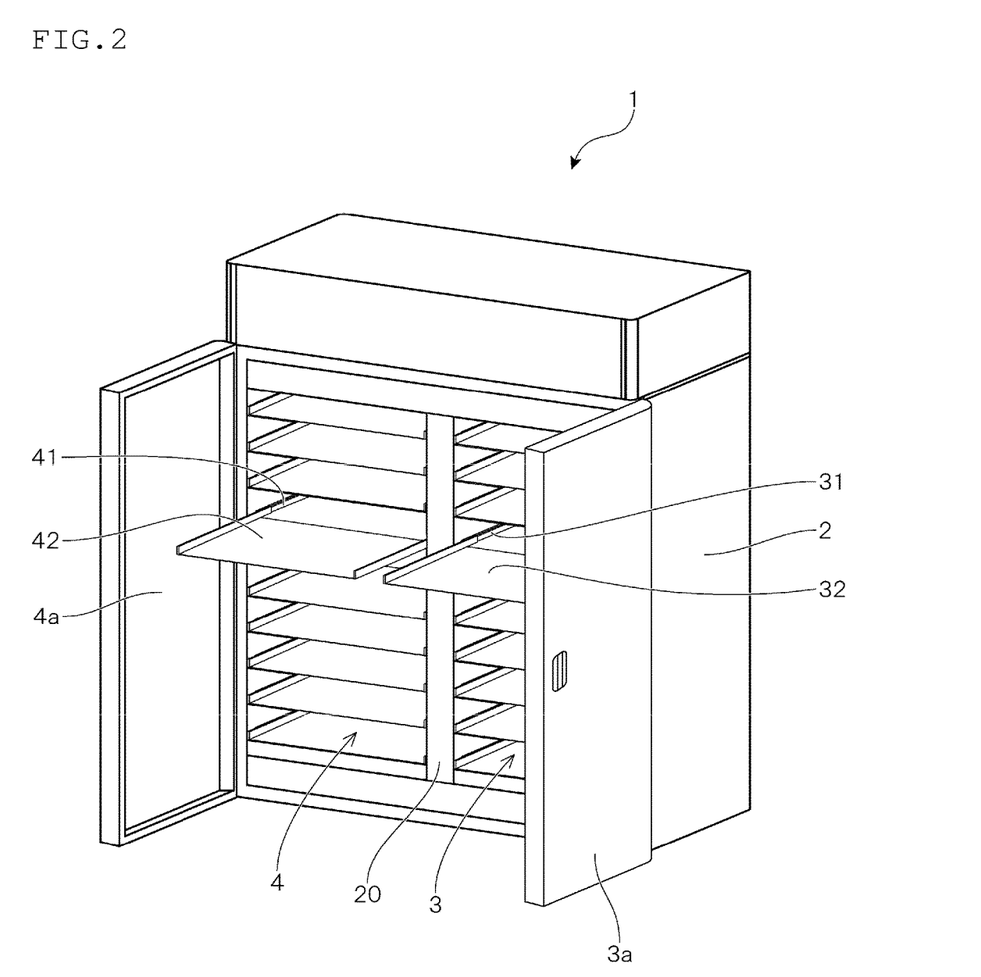
FIG. 2 is an appearance schematic view of the cell culture apparatus according to the embodiment of the present invention.

In the present embodiment, a cell culture apparatus 1 is an apparatus to store a plurality of cell culture units U in a multi-stage state and individually perform cell culture in each of the cell culture units U. FIG. 1 and FIG. 2 show appearance schematic views of the cell culture apparatus 1. In the cell culture apparatus 1, an inner portion of a casing 2 has a double tank structure divided into an incubating tank 3 and a cold insulation tank 4 which can be adjusted at a predetermined temperature, by an insulation wall 20. Further, the incubating tank 3 and the cold insulation tank 4 are provided with independently openable and closable front doors 3a and 4a, respectively.

Figure 3:
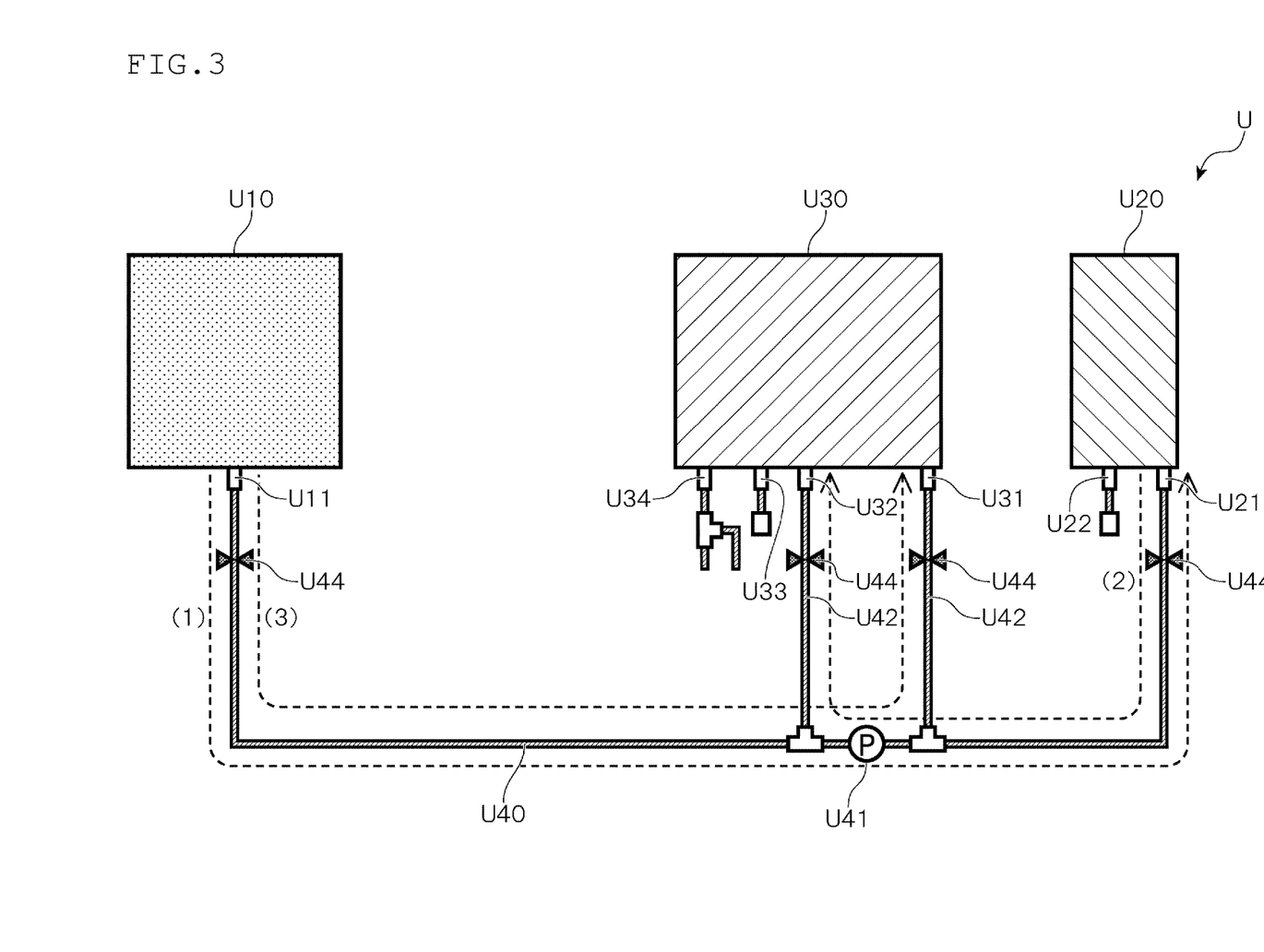
FIG. 3 is an explanatory view showing one example of a cell culture unit to be stored in the cell culture apparatus according to the embodiment of the present invention.

For example, as shown in FIG. 3, a cell culture unit U to be stored in the cell culture apparatus 1 comprises a first culture container U20 and a second culture container U30 for use in cell culture, a medium container U10 to supply a medium to the culture containers U20, U30, and a transfer tube U40 and culture container connecting tubes U42 to connect the containers U10, U20 and U30.

The first culture container U20 is a culture container into which cells are injected, to first perform cell culture, and is suitably usable as, for example, an activating culture container for use in the cell culture to activate the cells. In a case of activating floating cells such as lymphocytes by use of the first culture container U20 as the activating culture container, a substance such as an anti-CD3 antibody to activate the cells is immobilized in a solid phase on a bottom surface in the first culture container U20.

The second culture container U30 is a container into which, after the cell culture in the first culture container, a cell suspension in the first culture container is transferred, to perform the cell culture, and the second culture container is suitably usable as, for example, a proliferating culture container for use in the cell culture to proliferate the cells.

In this way, the first culture container U20 is used as the activating culture container, and the second culture container U30 is used as the proliferating culture container, thereby making it possible to suitably proliferate floating cells such as the lymphocytes.

In the present embodiment, these containers are connected to the transfer tube U40 in the order of the medium container U10, the second culture container U30 and the first culture container U20. It is to be noted that in a case where the containers are seen from a back side, the containers are connected to the transfer tube U40 in the order of the first culture container U20, the second culture container U30 and the medium container U10, and these orders are the same.

The medium container U10 comprises a port U11 for liquid delivery (including inward delivery and outward delivery), and is connected to the transfer tube U40 through the port U11.

The first culture container U20 comprises a port U21 for liquid delivery, and is connected to the transfer tube U40 through the port U21.

As shown in FIG. 3, it is preferable that the port U21 is disposed on the side of the transfer tube U40 in a peripheral edge portion of the first culture container U20 and most apart from the second culture container U30. Consequently, in delivering a content out from the first culture container U20, i.e., in transferring the cell suspension from the first culture container U20 to the second culture container U30, the first culture container U20 is tilted so as to dispose the port U21 downwardly, thereby making it possible to inhibit the cell suspension from remaining in the first culture container U20.

Furthermore, in removing bubbles which enter into the first culture container U20 in a process of the cell culture, for example, at a time of supplying the medium from the medium container U10 to the first culture container U20, the first culture container U20 is tilted to dispose the port U21 upwardly, whereby the bubbles which enter into the first culture container U20 can be collected in the vicinity of the port U21 and can easily be removed from the port U21.

The second culture container U30 comprises a port U31 and a port U32 for liquid delivery, one side end portions of two culture container connecting tubes U42 are connected to these ports respectively, and the other side end portions are connected to the transfer tube U40. A pump U41 is attached to a portion between connected portions of the culture container connecting tubes U42 in the transfer tube U40.

That is, the cell culture unit U comprises only one pump, and has a constitution in which the second culture container U30 is connected to the transfer tube U40 on both sides of the pump U41 by the culture container connecting tubes U42 to connect the second culture container U30 and the transfer tube U40.

As shown in FIG. 3, it is preferable that the port U31 is disposed on the side of the transfer tube U40 in a peripheral edge portion of the second culture container U30 and most apart from the medium container U10. Consequently, in delivering the content out from the second culture container U30, i.e., in transferring and collecting the cell suspension from the second culture container U30 to the emptied medium container U10, the second culture container U30 is tilted so as to dispose the port U31 downwardly, thereby making it possible to inhibit the cell suspension from remaining in the second culture container U30.

Furthermore, in removing bubbles which enter into the second culture container U30 in a process of the cell culture, for example, at a time of transferring the cell suspension from the first culture container U20 to the second culture container U30 or supplying the medium from the medium container U10 to the second culture container U30, the second culture container U30 is tilted to dispose the port U31 upwardly, whereby the bubbles which enter into the second culture container U30 can be collected in the vicinity of the port U31 and can easily be removed from the port U31.

There is not any special restriction on the number of the ports in each of these containers, and the number of the ports can be adjusted to be optional. In an example of FIG. 3, the first culture container U20 comprises a port U22 for cell injection in addition to the port U21. Furthermore, the second culture container U30 comprises a preliminary port U33 to inject a proliferation factor or the like and a sampling port U34 in addition to the ports U31 and U32.

When the liquid delivery is not performed between the containers, a flow channel from each container is closed with a closing member U44 such as a clip. That is, in the example of FIG. 3, the flow channel between each container and the pump U41 is stopped with the clip. Further, in performing the liquid delivery between the containers, the closing with the closing member U44 for the two containers between which the liquid delivery is performed is only released to open the flow channel, and the liquid delivery by the pump U41 is performed.

To perform the cell culture in the cell culture unit U constituted in this way, the cells are first injected into the first culture container U20 from the port U22.

Next, the pump U41 is operated, and by the pump U41, the medium is transferred from the medium container U10 to the first culture container U20 as shown in FIG. 3 (an arrow (1) in the same figure). Then, in the first culture container U20, the cell culture is performed for a predetermined period.

After the cell culture in the first culture container U20, the cell suspension is transferred from the first culture container U20 to the second culture container U30 by the pump U41 (an arrow (2) in the same figure), and next the medium is transferred from the medium container U10 to the second culture container U30 (an arrow (3) in the same figure).

At this time, the transfer of the cell suspension from the first culture container U20 to the second culture container U30 is performed via the culture container connecting tube U42 connected to the transfer tube U40 on a medium container U10 side of the pump U41.

Furthermore, the transfer of the medium from the medium container U10 to the second culture container U30 is performed via the culture container connecting tube U42 connected to the transfer tube U40 on a first culture container U20 side of the pump U41.

According to the cell culture unit U, it is possible to appropriately perform, by use of only one pump U41, transfers of three systems, i.e., the transfer of the medium from the medium container U10 to the first culture container U20, the transfer of the cell suspension from the first culture container U20 to the second culture container U30 and the transfer of the medium from the medium container U10 to the second culture container U30.

In general, the medium container U10 having gas barrier properties to oxygen and carbon dioxide is used so that a pH of the stored medium does not noticeably change in a culture period. Because, in order to avoid that a high-concentration carbonic acid gas included in the medium falls out in the air and that the concentration of the carbonic acid gas in the medium decreases to increase the pH, it is desirable to minimize leaking of carbon dioxide out from the medium container U10 as much as possible, and it is also desirable to prevent oxidation of the medium.

The first culture container U20 and the second culture container U30 are formed into a bag shape by use of a soft packaging member as a material, and partially or entirely have transparency so that the contents can be confirmed. Furthermore, these culture containers are required to have a gas permeability (an oxygen and carbon dioxide permeability) required for the cell culture, and are preferably used at 37° C. under a culture environment where a concentration of carbon dioxide is 5%. Furthermore, it is preferable that the culture containers have low cytotoxicity, low elution, and radiation sterilization suitability to achieve a high cell proliferating efficiency.

As a material of the culture container which satisfies these conditions, a polyethylene-based resin is preferable. Examples of this polyethylene-based resin include polyethylene, a copolymer of ethylene and α-olefin, a copolymer of ethylene and vinyl acetate, and ionomers in which ethylene, an acrylic acid or methacrylic acid copolymer and metal ions are used. Alternatively, polyolefin, a styrene-based elastomer, a polyester-based thermoplastic elastomer, a silicone-based thermoplastic elastomer, a silicone resin or the like is usable.

There is not any special restriction on a shape of each of the medium container U10, the first culture container U20 and the second culture container U30 and a shape of a containing section of the container, and in the example of FIG. 3, the container is formed into a rectangular shape. The container can be manufactured by sealing four sides of the container with a heat seal, or can be manufactured as an integrally formed bag by blow forming.

It is preferable that each port is disposed on the transfer tube U40 side, and it is also preferable that the containing section gradually narrows toward an attaching portion of the tube.

A material of the transfer tube U40 and the culture container connecting tubes U42 may suitably be selected in accordance with a use environment, but is preferably excellent in gas permeability. For example, there is usable a silicone rubber, a soft vinyl chloride resin, a polybutadiene resin, an ethylene-vinyl acetate copolymer, a chlorinated polyethylene resin, a polyurethane-based thermoplastic elastomer, a polyester-based thermoplastic elastomer, a silicone-based thermoplastic elastomer, a styrene-based elastomer, or the like. Furthermore, as the styrene-based elastomer, there is usable, for example, SBS (styrene-butadiene-styrene), SIS (styrene-isoprene-styrene), SEBS (styrene-ethylene-butylene-styrene), SEPS (styrene-ethylene-propylene-styrene), or the like.

In FIG. 3, for example, a silicone tube is used in a portion of the transfer tube U40 to which the pump U41 is attached, and a soft vinyl chloride resin tube is suitably usable in another portion thereof.

Furthermore, connection between the tubes in the transfer tube U40 can be performed with a luer connector or another coupling means. Furthermore, in the transfer tube U40, flow channel opening/closing means such as a pinch valve, a two-way stopcock or a three-way stopcock may be disposed.

There is not any special restriction on a type of pump U41, but a tube roller pump such as a peristaltic pump (R) is suitably usable because a closed system in the cell culture unit U is easy to be realized.

In the present embodiment, the cell culture unit U is stored in the cell culture apparatus 1, but the first culture container U20 and the second culture container U30 are stored in the incubating tank 3 in which a temperature is adjusted to be maintained at a temperature (e.g., 37° C.) suitable for the cell culture, and the medium container U10 is stored in the cold insulation tank 4 in which a temperature is adjusted to be maintained at a temperature (e.g., 4° C.) suitable for the storage of the medium.

Figure 4:
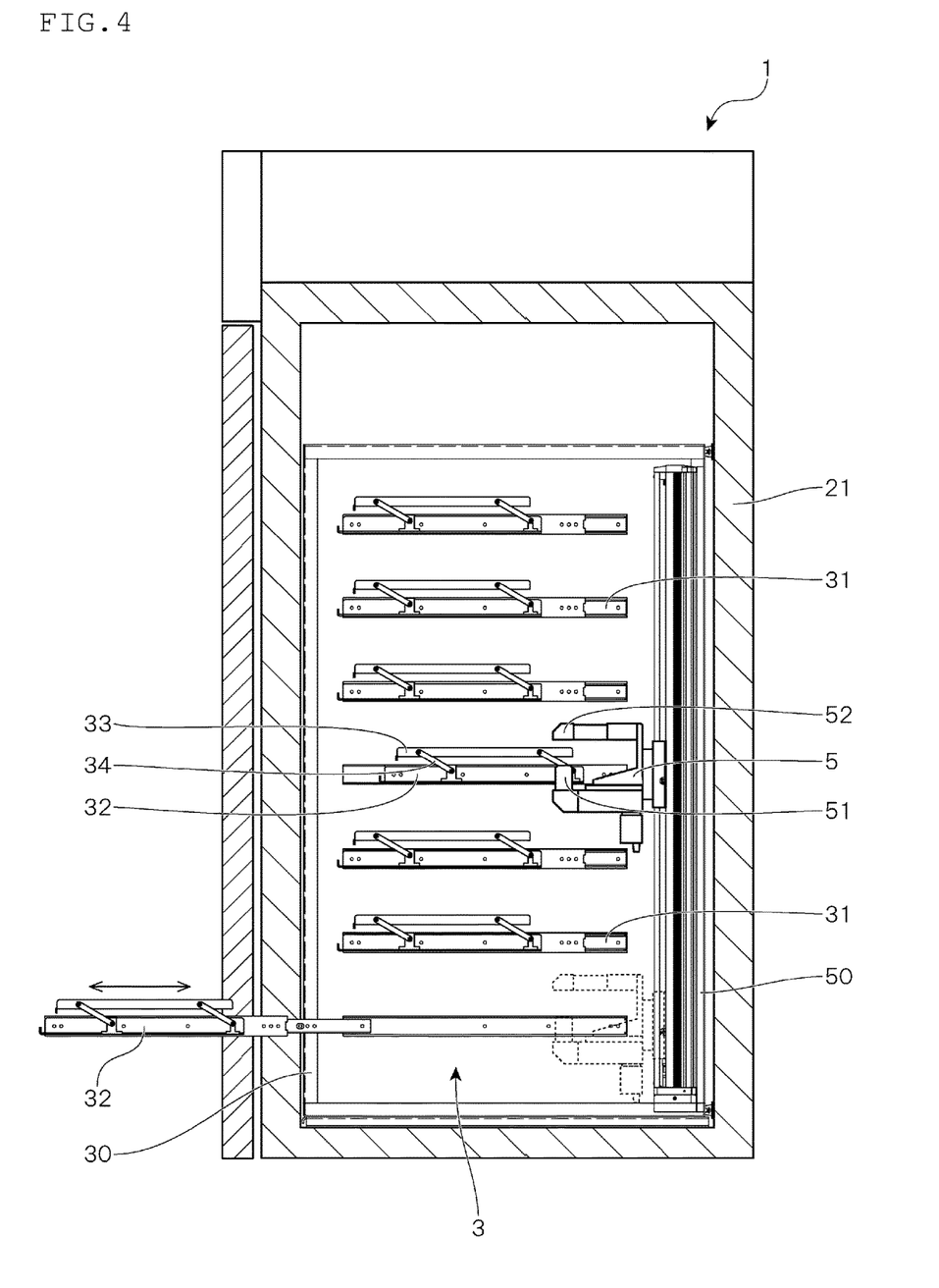
FIG. 4 is an explanatory view of a cross-sectional view showing an inner portion of an incubating tank of the cell culture apparatus according to the embodiment of the present invention.

As shown in FIG. 4, in the incubating tank 3 in which the first culture container U20 and the second culture container U30 are stored, an incubating tank side support frame 30 is disposed in which a plurality of slide rails 31 are arranged in a multi-stage state along a height direction. To each of the slide rails 31 arranged in the incubating tank side support frame 30, a culture container accommodating shelf 32 to accommodate the first culture container U20 and the second culture container U30 is slidably attached to be pulled out to a proximal side. Consequently, when the first culture container U20 and the second culture container U30 are mounted on or removed from the culture container accommodating shelf 32, the culture container accommodating shelf 32 is pulled out to the proximal side, thereby making it possible to easily perform such an operation.

It is to be noted that in an example shown in FIG. 4, the pump U41 and the closing member U44 constituting the cell culture unit U are attached to a proximal side of the culture container accommodating shelf 32, but illustration of the transfer tube U40 and others is omitted.

Furthermore, similarly in the cold insulation tank 4 in which the medium container U10 is stored, a cold insulation tank support frame 40 is disposed in which a plurality of slide rails 41 are arranged in a multi-stage state along a height direction. Then, to each of the slide rails 41 arranged in the cold insulation tank side support frame 40, a medium container accommodating shelf 42 to accommodate the medium container U10 is slidably attached to be pulled out to the proximal side. In consequence, when the medium container U10 is mounted on or removed from the medium container accommodating shelf 42, the medium container accommodating shelf 42 is pulled out to the proximal side, thereby making it possible to easily perform such an operation (see FIG. 5).

Figure 5:
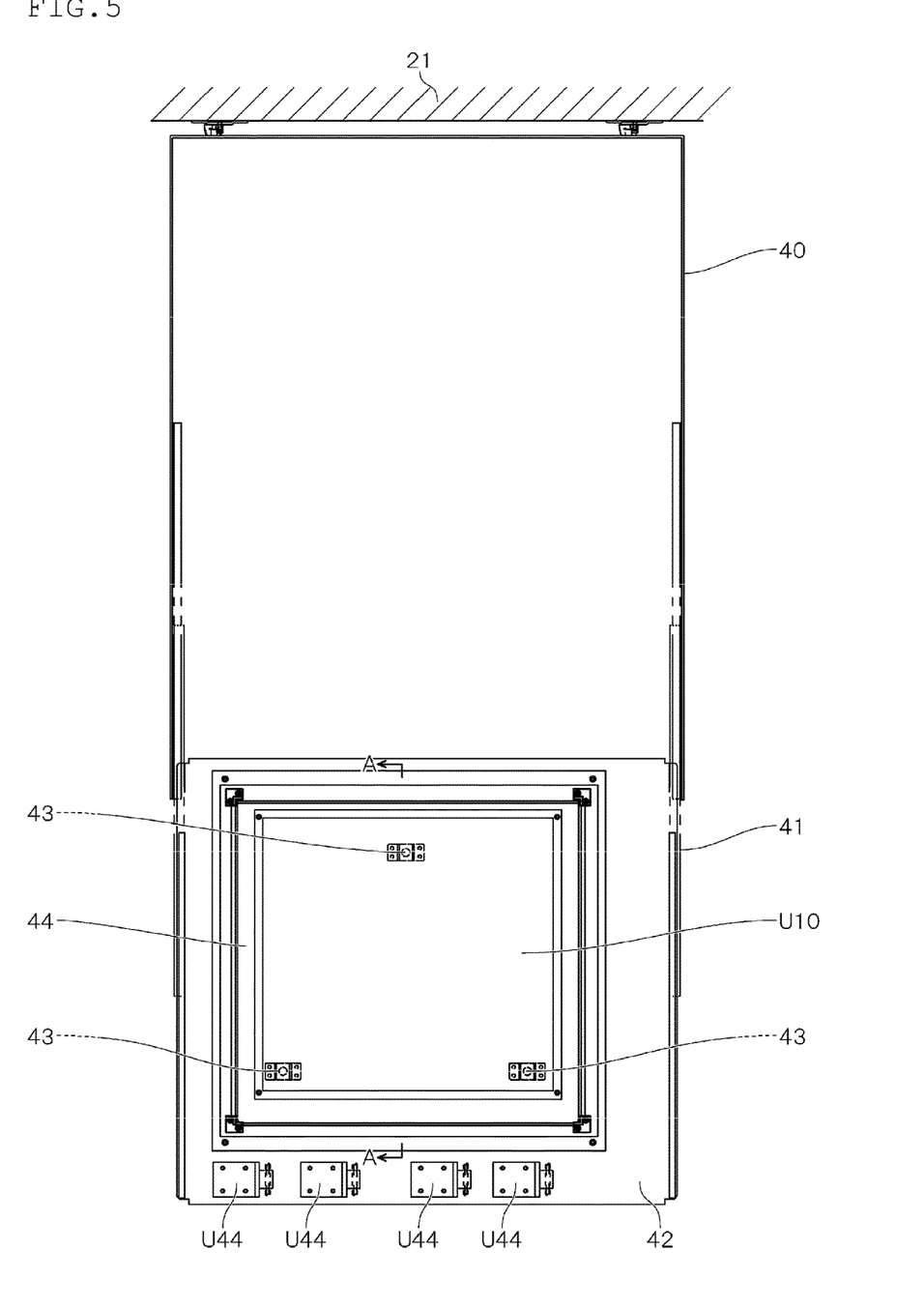
FIG. 5 is an explanatory view of a planar view showing a state where a medium container accommodating shelf of the cell culture apparatus according to the embodiment of the present invention is pulled out to a proximal side.

It is to be noted that FIG. 5 is a planar view showing a state where the medium container accommodating shelf 42 is pulled out to the proximal side, the closing members U44 constituting the cell culture unit U are attached to the proximal side of the medium container accommodating shelf 42, but illustration of the port U11 and the transfer tube U40 disposed in the medium container U10 is omitted.

Consequently, in the present embodiment, the culture container accommodating shelf 32 and the medium container accommodating shelf 42 form a pair and are disposed separately in the incubating tank 3 and the cold insulation tank 4 which are adjusted at a predetermined temperature, the first culture container U20 and the second culture container U30 are accommodated in the culture container accommodating shelf 32, and the medium container U10 is accommodated in the medium container accommodating shelf 42, whereby the plurality of cell culture units U can be stored in the multi-stage state. In consequence, according to the cell culture apparatus 1 of the present embodiment, under a temperature environment suitable for each of the first culture container U20, the second culture container U30 and the medium container U10, the plurality of cell culture units U are independently stored in the multi-stage state, and the cell culture can individually be performed in each of the cell culture units U.

It is to be noted that FIG. 2 shows a state where the culture container accommodating shelf 32 and the medium container accommodating shelf 42 form the pair and are pulled out to the proximal side. However, for the convenience in preparing the drawing, illustration of the cell culture units U to be stored in theses shelves, auxiliary devices and others is omitted.

Furthermore, in the present embodiment, the incubating tank side support frame 30 is disposed to be capable of freely being inserted into and taken out from the incubating tank 3 so that the culture container accommodating shelves 32 and the other auxiliary devices attached to the incubating tank side support frame 30 can be taken together with the incubating tank side support frame 30 out from the incubating tank 3. Similarly, the cold insulation tank side support frame 40 is also disposed to be capable of freely being inserted into and taken out from the cold insulation tank 4, and hence the medium container accommodating shelves 42 and the other auxiliary devices attached to the cold insulation tank side support frame 40 can be taken together with the cold insulation tank side support frame 40 out from the cold insulation tank 4. In consequence, the devices disposed in the casing 2 of the cell culture apparatus 1 can be taken out from and disposed in the respective tanks, together with the support frames 30 and 40.

According to such a constitution of the cell culture apparatus 1, for example, when maintenance or the like of the cell culture apparatus 1 is performed, the devices disposed in the casing 2 can be taken outside together with the support frames 30 and 40, and an operation space on the side of the casing 2 can be acquired, so that an operability in performing the maintenance or the like of the cell culture apparatus 1 can improve. Furthermore, for example, at a time of generation of an abnormality in the cell culture apparatus 1, the cell culture units U are not taken out one by one, but all the cell culture units U are taken out together with the support frames 30 and 40, thereby making it possible to cope with the problem in a short time.

The support frames 30 and 40 are taken out from the casing 2, and then these frames may be mounted on a cart to move, but the support frames 30 and 40 may be provided with moving means such as casters so that these frames are easily movable.

Furthermore, in the present embodiment, in the cell culture apparatus 1 in which the plurality of cell culture units U are stored in the cell culture apparatus 1 and the cell culture is performed in each of the cell culture units U, a measurement unit 5 to measure a progressive state of the cell culture in the first culture container U20 and the second culture container U30 provided in each of the cell culture units U is interposed between a back panel part 21 of the casing 2 of the cell culture apparatus 1 and the culture container accommodating shelf 32 (see FIG. 4).

The measurement unit 5 comprises an imaging part 51 which images portions to be measured of the culture containers U20, U30, and there is not any special restriction on its specific constitution as long as the progressive state of the cell culture can be measured, for example, by analyzing imaging data and calculating the number of the cells, a cell density or the like. In the example shown in the drawing, the measurement unit 5 comprises the imaging part 51 having a CCD camera and an objective lens, and an illuminating part 52 disposed to face the imaging part 51, and portions to be imaged of the culture containers U20, U30 can be imaged from the downside, while illuminating the portions to be imaged of the culture containers U20, U30 with illuminating light from the upside.

Although not especially shown in the drawing, in a case where the first culture container U20 and the second culture container U30 are formed into the bag shape by use of the soft packaging member as the material as in the present embodiment, the measurement unit 5 may comprise a pressing member which presses the portions to be imaged so that inner portions of the culture containers U20, U30 can clearly be imaged in a state where bends of the portions are eliminated, when the portions to be imaged of the culture containers U20, U30 are imaged.

The measurement unit 5 is disposed so as to be movable up and down in the casing 2 so that the progressive state of the cell culture can be measured in each of all the cell culture units U stored in the cell culture apparatus 1. For example, in a support pillar 50 attached to the incubating tank side support frame 30, the measurement unit is disposed so as to be movable up and down by a power source such as a motor.

Figure 8:
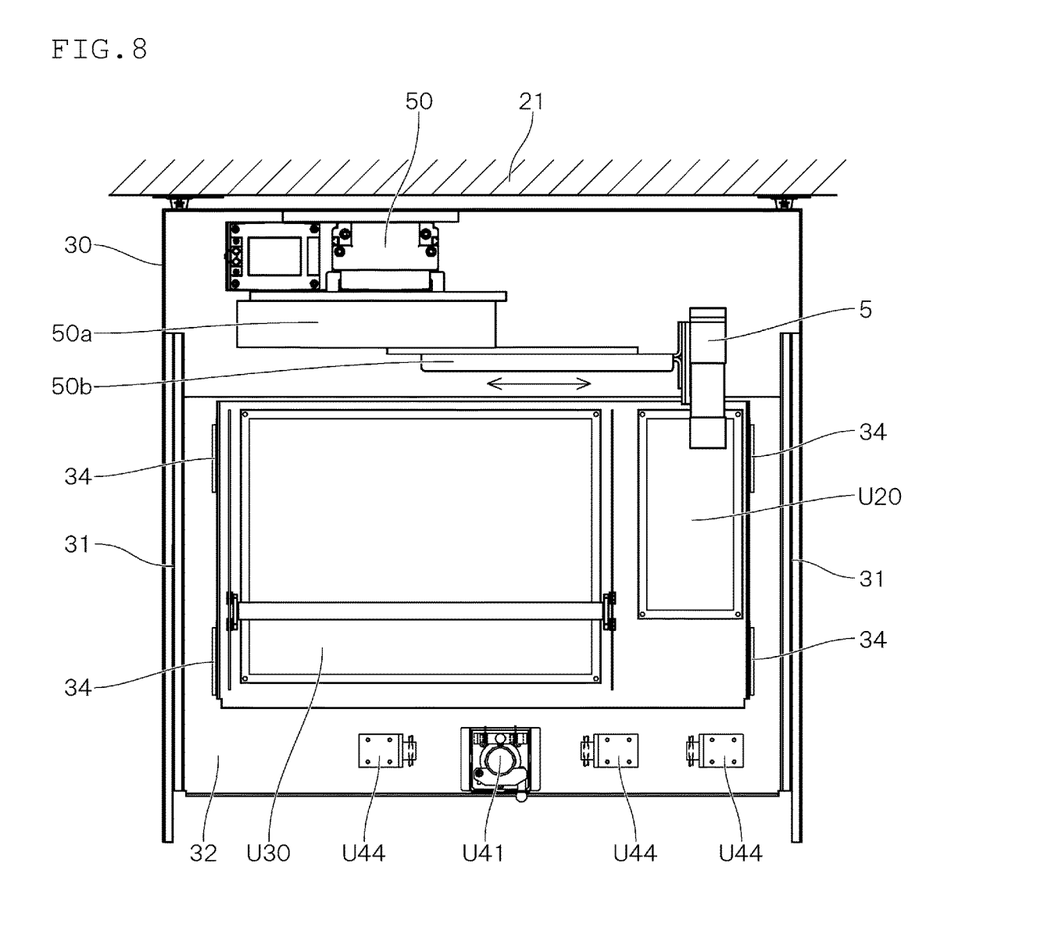
FIG. 8 is an explanatory view of a planar view showing a state where the culture container accommodating shelf of the cell culture apparatus according to the embodiment of the present invention is slid and moved.
Figure 9:
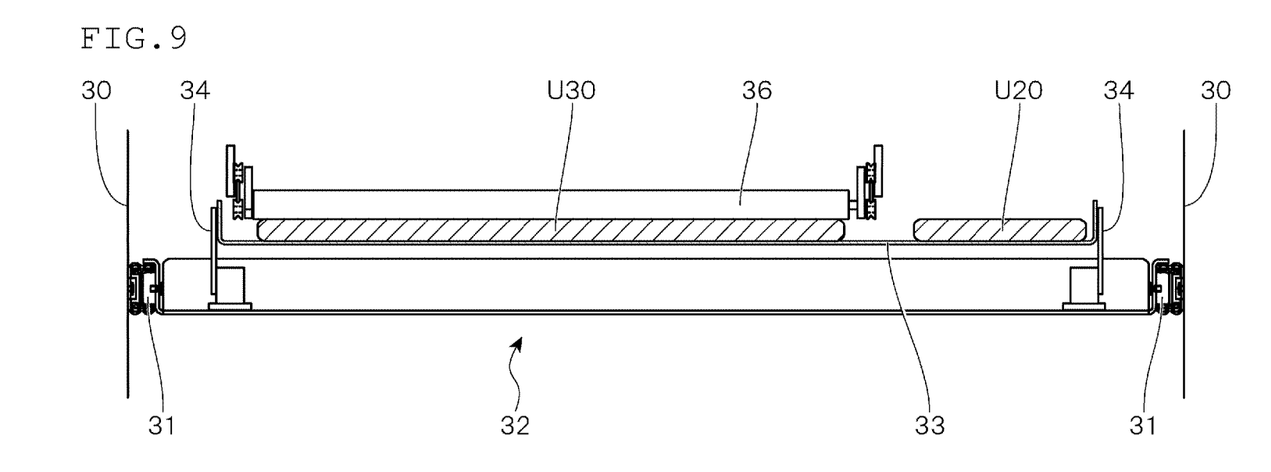
FIG. 9 is a cross-sectional view along the line B-B of FIG. 6.

Furthermore, in the present embodiment, the cell culture unit U comprises the first culture container U20 and the second culture container U30, but the measurement unit 5 can be adjusted to be also movable in a horizontal direction as shown by arrows in FIG. 8 so that the progressive state of the cell culture in each of the culture containers U20, U30 can be measured.

In an example shown in FIG. 8, the measurement unit 5 is held by guide members 50a and 50b so as to be movable in the horizontal direction, and the guide members 50a and 50b are vertically movably attached to the support pillar 50, but a specific mechanism is not limited to this example.

Alternatively, in the present embodiment, the culture container accommodating shelf 32 which accommodates the first culture container U20 and the second culture container U30 can not only be pulled out to the proximal side but also be slid toward a distal side. Consequently, when the measurement unit 5 moves in the casing 2 to reach a measurement position of the cell culture unit U which is the measurement subject, the culture container accommodating shelf 32 which accommodates the first culture container U20 and the second culture container U30 of the cell culture unit U moves toward the measurement unit 5 (see FIG. 4 and FIG. 8). Successively, when the portions to be measured of the first culture container U20 and the second culture container U30 accommodated in the culture container accommodating shelf 32 come in an imaging range of the imaging part 51 provided in the measurement unit 5, the measurement of the progressive state of the cell culture by the measurement unit 5 is started.

In consequence, the progressive state of the cell culture in the cell culture unit of the measurement subject can be measured by a single measurement unit 5 in each of all the cell culture units U without interfering with an adjacent cell culture unit U.

Figure 6:
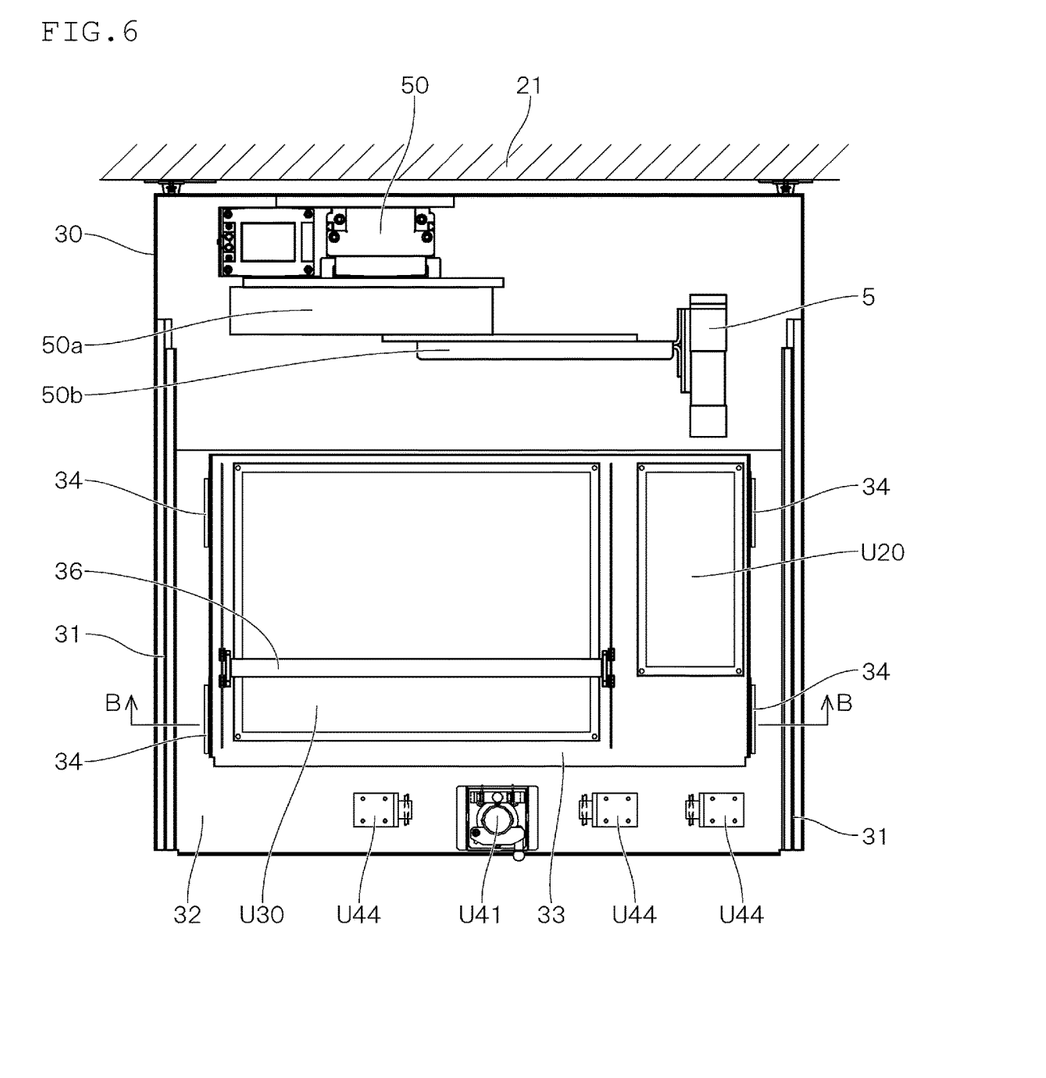
FIG. 6 is an explanatory view of a planar view showing a state where the medium container accommodating shelf of the cell culture apparatus according to the embodiment of the present invention is slid and moved.
Figure 7:
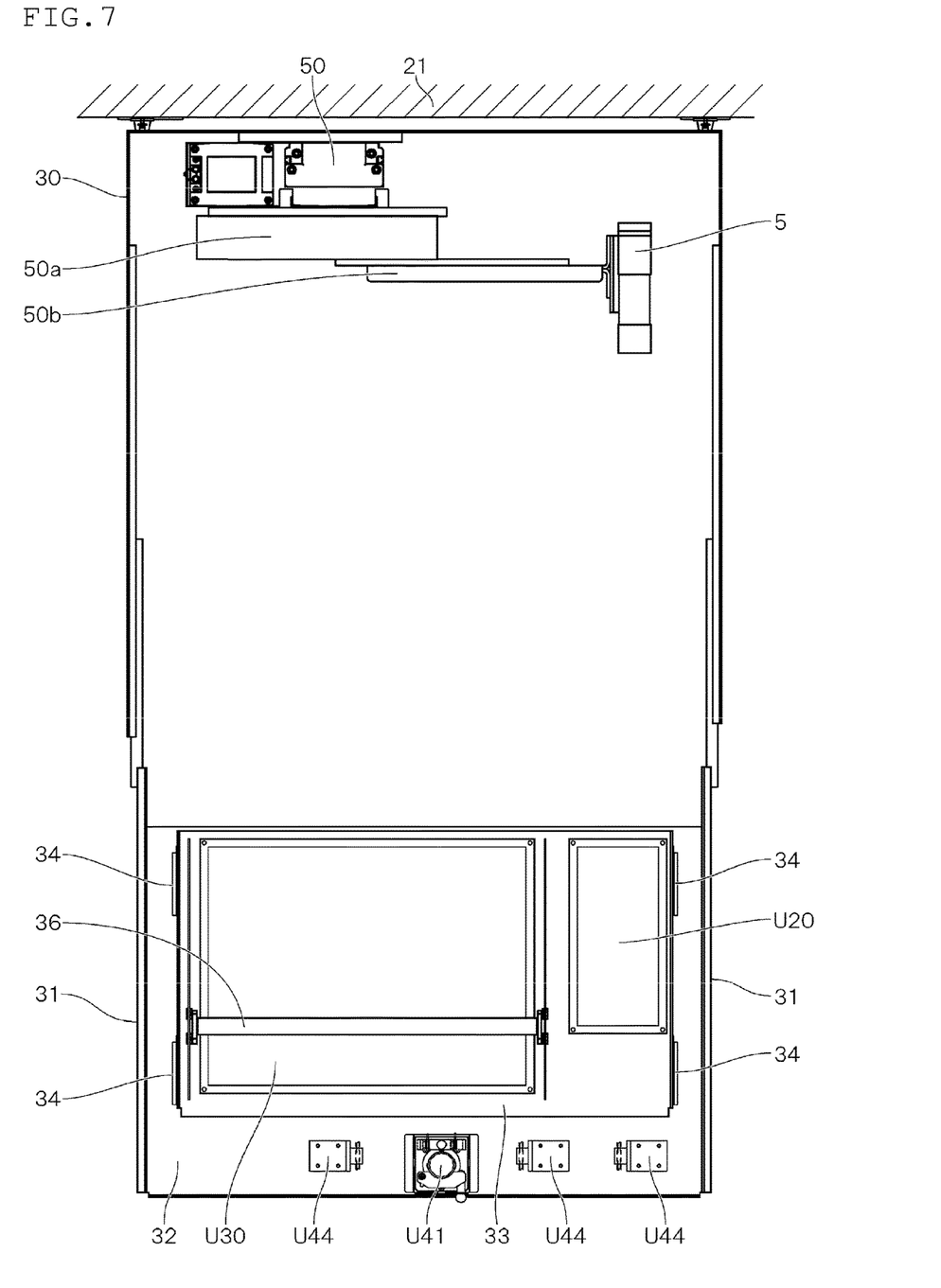
FIG. 7 is an explanatory view of a planar view showing a state where a culture container accommodating shelf of the cell culture apparatus according to the embodiment of the present invention is slid and moved.

Here, FIG. 6 to FIG. 8 are planar views showing states where the culture container accommodating shelf 32 is slid to move. When the culture container accommodating shelf 32 is pulled out to the proximal side from the state shown in FIG. 6, it becomes the state shown in FIG. 7. This state corresponds to a position of the culture container accommodating shelf 32 shown in a lowermost stage in FIG. 4. Successively, when the culture container accommodating shelf moves from the state shown in FIG. 6 toward the measurement unit 5, it becomes the state shown in FIG. 8. This state corresponds to a position of the culture container accommodating shelf 32 shown in the fourth stage from the bottom in FIG. 4.

It is to be noted that in an example shown in FIG. 6 to FIG. 8, the pump U41 and the closing members U44 which constitute the cell culture unit U are attached to the proximal side of the culture container accommodating shelf 32, but there is omitted illustration of the ports U21 and U22 disposed in the first culture container U20, the ports U31, U32, U33 and U34 disposed in the second culture container U30, the transfer tube U40 and the culture container connecting tubes U42.

Furthermore, as described above, in transferring the content of the first culture container U20 or the second culture container U30 from its port U21 or U31, the culture containers U20, U30 are tilted so as to dispose the ports U21, U31 downwardly, whereby the content can be inhibited from remaining. Additionally, in removing the bubbles which enter into the culture containers U20, U30, the culture containers U20, U30 are tilted to dispose the ports U21, U31 upwardly, whereby the bubbles which enter into the culture containers U20, U30 can be collected in the vicinities of the ports U21, U31 and can easily be removed.

In the present embodiment, for the purpose of enabling this operation, the culture container accommodating shelf 32 comprises a swing plate 33 as tilting means for tilting the first culture container U20 and the second culture container U30 so that the ports U21, U31 are positioned at lower positions or upper positions. Then, the culture containers U20, U30 are mounted on the swing plate 33, whereby the culture containers U20, U30 are accommodated in the culture container accommodating shelf 32.

In the present embodiment, two swing plates 33 are attached to side edges which face four swing arms 34 supporting the swing plates 33. Then, the swing arms 34 are turned to swing the swing plates 33, thereby generating tilt to a horizontal plane in culture containers U20, U30, but a specific constitution of the swing plate 33 is not limited to this example. The culture containers U20, U30 may only be tilted with a height difference so that the ports U21, U31 are disposed at the lower positions or upper positions in accordance with the positions of the ports U21, U31 disposed in the culture containers U20, U30.

It is to be noted that in the present embodiment, the swing plates 33 supported by the swing arms 34 are provided as the tilting means, but the culture containers U20, U30 may be mounted on a plate which is constituted so as to turn and tilt in a predetermined periaxial direction and this plate may be defined as tilting means, as long as the culture containers U20, U30 can be tilted as described above.

Alternatively, as shown in FIG. 6 to FIG. 9, in the swing plate 33, a stirring roller 36 to stir the content of the second culture container U30 may be disposed as required. There is not any special restriction on a specific constitution of the stirring roller 36, as long as the stirring roller pressed onto an upper surface of the second culture container U30 reciprocatingly moves and can stir the content while bending and deforming the second culture container U30 made of the soft packaging member.

It is to be noted that in FIG. 4, illustration of the stirring roller is omitted.

Furthermore, in removing the bubbles which enter into the first culture container U20 or the second culture container U30 from its port U21, U31, the removed bubbles can be transferred through the transfer tube U40 to flow into the medium container U10, by releasing, for example, the closing with the closing member U44 between the first culture container U20 or the second culture container U30 and the medium container U10 to open the flow channel, and operating the pump U41. At this time, for the purpose of inhibiting the content of the first culture container U20 or the second culture container U30 from also flowing into the medium container U10 together with the bubbles, the medium container accommodating shelf 42 in which the medium container U10 is accommodated comprises weight detecting means 43 for detecting a weight change of the medium container U10 in the present embodiment (see FIG. 5 and FIG. 10).

That is, when the content of the first culture container U20 or the second culture container U30 passes through the transfer tube U40 together with the bubbles and is transferred to the medium container U10 side, the weight increases due to the content. When the weight increase at this time is detected and the pump U41 is automatically or manually stopped to end a transfer operation of the bubbles, the contents of the culture containers U20, U30 can be inhibited from flowing into the medium container U10. Then, the pump U41 is operated in reverse, whereby the content remaining in the transfer tube U40 can be returned to the culture containers U20, U30 and the content is not wasted.

It is to be noted that a period from when the weight increase is detected until the pump U41 stops and a period for which the pump U41 is operated in reverse can suitably be set in accordance with a volume of the transfer tube U40, a liquid delivery rate of the pump U41 and the like.

Furthermore, in the present embodiment, the medium container accommodating shelf 42 comprises the weight detecting means 43, but when the culture container accommodating shelf 32 comprises weight detecting means to detect a weight decrease when the content of the first culture container U20 or the second culture container U30 flows outside, thereby automatically or manually stopping the transfer operation of the bubbles, the contents of the culture containers U20, U30 can be inhibited from flowing into the medium container U10.

Furthermore, in the present embodiment, the medium container U10 is placed on a tray 44, and the medium container U10 is accommodated in the medium container accommodating shelf 42 via the tray 44. That is, the medium container U10 is not mounted directly on the medium container accommodating shelf 42, but the medium container U10 is placed on the tray 44 and is accommodated together with the tray 44 in the medium container accommodating shelf 42.

Consequently, for example, when performing an operation of storing the cell culture unit U in the cell culture apparatus 1, the first culture container U20 and the second culture container U30 can be placed on the tray 44 together with the medium container U10 and then they can be carried. In consequence, the tray 44 is disposed on the medium container accommodating shelf 42 to accommodate the medium container U10, and then the first culture container U20 and the second culture container U30 can be taken out from the tray 44 and can be mounted on the culture container accommodating shelf 32, whereby these series of operation can efficiently be performed.

Figure 10:
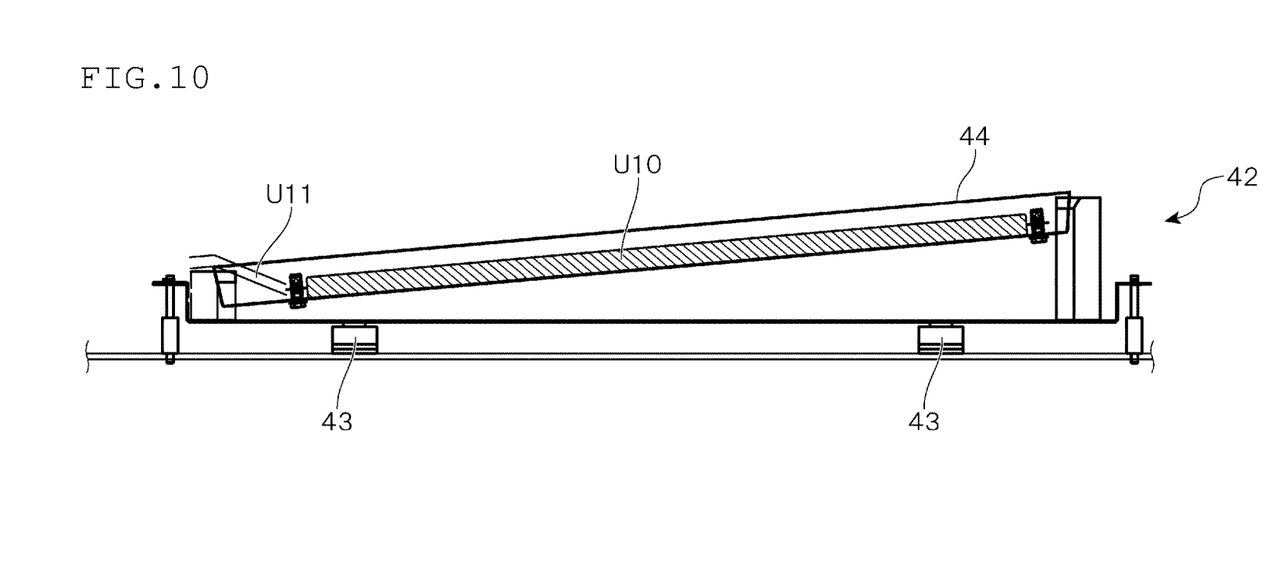
FIG. 10 is a cross-sectional view along the line A-A of FIG. 5.

Furthermore, in accommodating the medium container U10 in the medium container accommodating shelf 42 via the tray 44, it is preferable to tilt the tray 44 so that a side on which the port U11 of the medium container U10 is disposed becomes lower as shown in FIG. 10. Consequently, when the medium is supplied from the medium container U10 to the culture containers U20, U30, the medium can be inhibited from remaining in the medium container U10.

The present invention has been described above with reference to the preferable embodiment, but needless to say, the present invention is not limited to the above-mentioned embodiment, and it is possible to implement various modifications in the gist of the present invention.

For example, the cell culture unit U to be stored in the cell culture apparatus 1 is not limited to the above-mentioned example. The unit may only comprise a culture container into which, together with a cell (a culture cell) that is a culture target, a medium prepared to culture the cell is supplied and the cell culture is performed, and a medium container to supply the medium to the culture container.

Alternatively, there is not any special restriction on the number of the medium containers to be connected, and the cell culture unit U can be constituted by connecting at least one medium container to the transfer tube. Furthermore, the cell culture unit U can be constituted by connecting, to the transfer tube, a collecting container to collect a content (a cell suspension) of the culture container in which the cell culture is ended.

Furthermore, the above-mentioned embodiment, there has been described the example where the inner portion of the casing of the cell culture apparatus 1 has the double tank structure divided into the incubating tank 3 and the cold insulation tank 4 by the insulation wall 20, but there is not any special restriction on a specific constitution of each tank 3 or 4, as long as the culture container accommodating shelf 32 and the medium container accommodating shelf 42 form a pair and are disposed separately in the incubating tank 3 and the cold insulation tank 4. For example, although not especially shown in the drawing, the cell culture apparatus 1 may have a constitution in which a casing forming the incubating tank 3 and a casing forming the cold insulation tank 4 are independently disposed or these casings are coupled.

There are invoked herein all contents of the literature described in this description and the Japanese application description on the basis of which the priority of the present application under the Paris convention is claimed.

INDUSTRIAL APPLICABILITY

The present invention is suitably utilizable in a regenerative therapy, immunotherapy, antibody medicine production or the like to culture a large amount of cells in a closed system.

REFERENCE SIGNS LIST 1 cell culture apparatus
2 casing
20 insulation wall
3 incubating tank
30 incubating tank side support frame
31 slide rail
32 culture container accommodating shelf
33 swing plate
34 swing arm
4 cold insulation tank
40 cold insulation tank side support frame
41 slide rail
42 medium container accommodating shelf
43 weight detecting means
44 tray
5 measurement unit
U cell culture unit
U10 medium container
U20 first culture container (culture container)
U30 second culture container (culture container)
U40 transfer tube
U41 pump

The invention claimed is:
1. A cell culture apparatus comprising:
a plurality of cell culture units each comprising at least a culture container to which a medium is supplied together with cells to perform cell culture and a medium container to supply the medium to the culture container, in which the culture container and the medium container are connected by a transfer tube, and individually performing the cell culture in each of the cell culture units,
a support frame in which a plurality of slide rails are arranged in a multi-stage state along a height direction,
a casing in which the support frame is disposed, a culture container accommodating shelf in which the culture container is accommodated is slidably attached to each of the slide rails so as to allow the culture container accommodating shelf to slide toward a proximal side and a distal side of the casing, and a measurement unit comprising an imaging part having a camera is disposed so as to be movable up and down between a back panel part of the casing and the culture container accommodating shelf, wherein when the measurement unit reaches a measurement position of each cell culture unit that is a measurement subject, the culture container accommodating shelf which accommodates the culture container provided in the cell culture unit slides toward the measurement unit so that portions to be measured of the culture containers provided in the cell culture unit come in an imaging range of the imaging part.

2. The cell culture apparatus according to claim 1, wherein the measurement unit is disposed so as to be movable also in a horizontal direction.

3. The cell culture apparatus according to claim 1, comprising:

an incubating tank in which the culture containers are stored; and a cold insulation tank in which the medium container is stored, wherein in each of the incubating tank and the cold insulation tank, there are disposed an incubating tank side support frame and a cold insulation tank side support frame in each of which a plurality of slide rails are arranged in a multi-stage state along a height direction, the culture container accommodating shelf is slidably attached to each of the slide rails arranged in the multi-stage state in the incubating tank side support frame, and a medium container accommodating shelf to accommodate the medium container is slidably attached to each of the slide rails arranged in the multi-stage state in the cold insulation tank side support frame, and the culture container accommodating shelf and the medium container accommodating shelf form a pair and are disposed separately in the incubating tank and the cold insulation tank.

4. The cell culture apparatus according to claim 3, wherein an inner portion of the casing has a double tank structure divided into the incubating tank and the cold insulation tank by an insulation wall.

5. The cell culture apparatus according to claim 3, wherein the incubating tank side support frame and the cold insulation tank side support frame are disposed to be capable of being inserted into and taken out from the incubating tank and the cold insulation tank, respectively.

6. The cell culture apparatus according to claim 3, wherein the culture container accommodating shelf or the medium container accommodating shelf comprises weight detecting means, and in removing bubbles which enter into the culture containers in a process of the cell culture, the bubbles are transferred to the medium container through the transfer tube, and the weight detecting means provided in the culture container accommodating shelf or the medium container accommodating shelf detects a weight change of the culture container or the medium container to end a transfer operation of the bubbles.

7. The cell culture apparatus according to claim 6, wherein a pump attached to the transfer tube is operated to perform the transfer operation of the bubbles, the pump is stopped to end the transfer operation of the bubbles, and then the pump is operated in reverse, whereby a content in the transfer tube is returned to the culture containers.

8. The cell culture apparatus according to claim 3, wherein the medium container is placed on a tray, and the medium container is accommodated in the medium container accommodating shelf via the tray.

9. The cell culture apparatus according to claim 1, wherein the culture container accommodating shelf comprises tilting means for tilting the culture containers so that ports for liquid delivery provided in the culture containers are positioned at lower positions or upper positions.

10. The cell culture apparatus according to claim 9, wherein the tilting means are swing plates supported by swing arms.

* * * * *